United States Patent
Wadsworth et al.

(10) Patent No.: US 8,070,026 B2
(45) Date of Patent: Dec. 6, 2011

(54) ROTATING AND PIVOTING BELT CLIP THAT CAN BE USED AS A STAND

(75) Inventors: John Wadsworth, Burbank, CA (US); David Fuge, Apple Valley, CA (US)

(73) Assignee: Belkin International, Inc., Compton, CA (US)

( * ) Notice: Subject to any disclaimer, the term of this patent is extended or adjusted under 35 U.S.C. 154(b) by 878 days.

(21) Appl. No.: 11/959,896

(22) Filed: Dec. 19, 2007

(65) Prior Publication Data

US 2008/0156836 A1   Jul. 3, 2008

Related U.S. Application Data

(60) Provisional application No. 60/877,583, filed on Dec. 28, 2006.

(51) Int. Cl.
*A45F 5/00* (2006.01)

(52) U.S. Cl. ......... 224/197; 224/666; 224/269; 224/930

(58) Field of Classification Search .......... 224/197, 224/269, 666, 930
See application file for complete search history.

(56) References Cited

U.S. PATENT DOCUMENTS

| | | | | |
|---|---|---|---|---|
| 4,828,153 A | * | 5/1989 | Guzik et al. | 224/242 |
| 5,097,997 A | * | 3/1992 | Kipnis et al. | 224/269 |
| 6,029,871 A | * | 2/2000 | Park | 224/197 |
| 6,443,340 B1 | | 9/2002 | Chung et al. | |
| 7,110,802 B1 | * | 9/2006 | Kim et al. | 455/575.6 |
| 2005/0174727 A1 | * | 8/2005 | Thomas et al. | 361/681 |
| 2005/0236446 A1 | * | 10/2005 | Sims et al. | 224/269 |
| 2005/0279617 A1 | | 12/2005 | Han | |
| 2006/0140395 A1 | | 6/2006 | Kim | |
| 2006/0243772 A1 | * | 11/2006 | Sirichai et al. | 224/666 |

FOREIGN PATENT DOCUMENTS

| | | |
|---|---|---|
| EP | 1675271 | 6/2006 |
| JP | 04-328938 | 11/1992 |
| JP | 11-150589 | 6/1999 |
| JP | 3079536 | 6/2001 |
| JP | 2002-120655 | 4/2002 |
| JP | 2006-203520 | 8/2006 |
| JP | 2006-279970 | 10/2006 |
| TW | 578476 | 3/2004 |
| TW | M274728 | 9/2005 |
| TW | M274828 | 9/2005 |
| TW | M281487 | 12/2005 |
| TW | M288065 | 2/2006 |

* cited by examiner

*Primary Examiner* — Justin Larson
*Assistant Examiner* — Adam Waggenspack
(74) *Attorney, Agent, or Firm* — O'Melveny & Myers LLP

(57) ABSTRACT

A belt clip apparatus is provided that attaches to a case for a portable electronic device (e.g., a music player, video player, cell phone, etc.) that both swivels and pivots on two different axes. Such a clip can attach to an article of clothing and allow the user to view the screen and access the controls of an electronic device without having to first remove the device from the article of clothing. In one embodiment, the apparatus can stand on a flat surface in either an angled portrait or landscape orientation when attached to the case, thereby allowing the user to choose the optimal orientation for accessing the controls or viewing a screen on a portable device mounted within the attached case. The angle formed between the case and the belt clip can be varied so that the user can optimize the viewing angle of the attached portable electronic device.

18 Claims, 4 Drawing Sheets

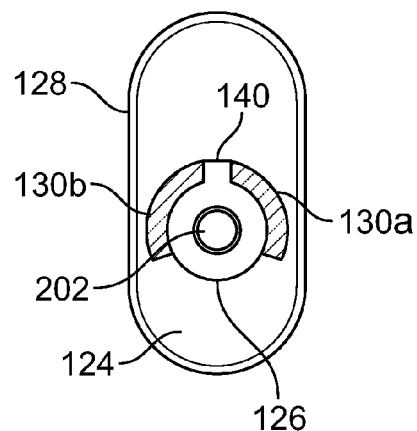
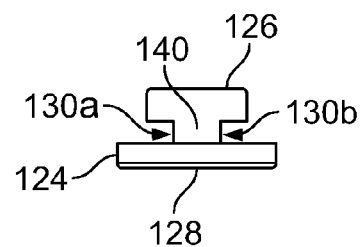
FIG. 2A            FIG. 2B
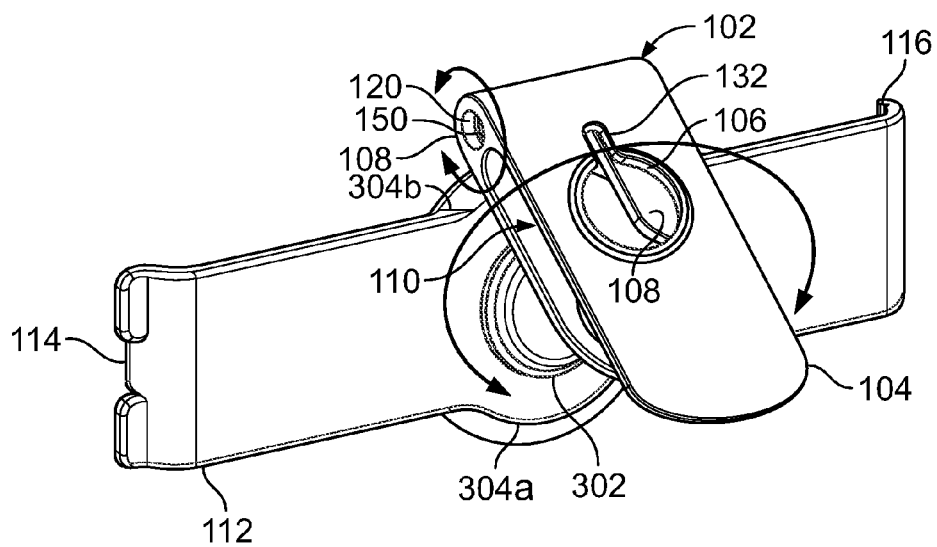
FIG. 3

ROTATING AND PIVOTING BELT CLIP THAT CAN BE USED AS A STAND

RELATED APPLICATION DATA

This application claims the benefit, pursuant to 35 U.S.C. §119(e), of U.S. provisional application Ser. No. 60/877,583, filed Dec. 28, 2006.

BACKGROUND OF THE INVENTION

1. Field of the Invention

The present invention relates generally to a belt clip for a portable electronic device and relates particularly to a belt clip that can swivel and pivot with respect to a case for the portable electronic device so that the belt clip may function as a stand when the electronic device is placed on a flat surface.

2. Description of Related Art

A belt clip is a known structure used to attach a portable electronic device or object to the belt of a user, allowing the user to carry the device on his belt. Examples of such portable electronic devices having belt clips include cell phones, pagers, music players (e.g., mp3, WMA, AAC, etc.) and/or video players, and CD players. One typical belt clip design has an elongated member secured at one end to the top of the back of a housing of a device (or a container holding the device) to form a clip with the back of the housing, such that a user's belt can be positioned between the elongated member and the housing. Often, the elongated member is hinged to the back of the housing, and biased (e.g., by way of a spring) against the back surface of the housing to retain the user's belt between the elongated member and the housing. The bottom of the elongated member may have a hook to facilitate retention of the belt.

Belt clips are often removably attached to the housing of a portable electronic device by a slidable member coupled to the belt clip having edges that can be positioned into grooves of the housing. This allows a user to remove the belt clip if it is not needed and to temporarily remove the device to view the screen or controls on the face of the device, or in the case of a cellular telephone, to place the phone to the user's ear. A drawback of such a belt clip, however, is that it requires additional user steps to detach and attach the belt clip each time the user needs to view the screen or access controls on the face of the device.

Another drawback of such a belt clip is that it is often rigidly held to the user's body, which greatly minimizes the amount of possible movement of the device (attached to the belt clip) relative to the user's body position, and often makes wearing the device uncomfortable. This is especially true when a user is seated and the electronic device digs into the top of the user's thigh.

Yet another drawback of such a belt clip is that it does not provide the ability to place a device (attached to the belt clip) on a flat surface in an angled, semi-vertical position in either a portrait or a landscape orientation so that the user can view videos and screen images in their optimal orientation.

Accordingly, there is a need for a system and method of fastening a portable electronic device to a belt clip that would allow the user to swivel, pivot, and/or tilt the device to easily view the screen of the device without having to first remove the portable electronic device from the user's belt. There is also a need for a belt clip that, when placed on a flat surface, can affix the attached portable electronic device in a semi-vertical position in either a portrait or a landscape orientation. Such a system would reduce the need for the user to remove the portable electronic device from the user's belt and/or the belt clip to view the screen or access controls and would eliminate the need for a separate case or device to hold the portable electronic device in an angled upright position, thus providing an improvement over currently available belt clips.

SUMMARY OF THE INVENTION

The present invention provides a belt clip for a portable electronic device (e.g., a music player, video player, personal digital assistant, cell phone, etc.) that both swivels and pivots on two different axes. Such a clip can be used, for example to view the screen and access the controls of the electronic device without having to first remove the electronic player from the user's belt or a case which the device may be mounted in. While the belt clip is attached to a portable electronic device, the device can stand on a flat surface in either an angled portrait or landscape orientation, thereby allowing the user to choose the optimal orientation for accessing the controls or viewing a screen on the portable electronic device mounted within the attached case. The angle formed between the electronic device and the belt clip can be varied so that the user can optimize the viewing angle when the belt clip is used as a stand. This same function allows the case to rotate slightly away from the belt clip automatically when the user takes a seated position with the belt clip is attached to the case and to an article of clothing, thereby preventing the case from digging into the top of the user's thigh.

In one embodiment of the present invention, there is provided a belt clip assembly for a portable electronic device comprising a clip body and a mounting bracket with a circular-shaped swivel mount attached in the center. The swivel mount can rotate in a clockwise and/or counterclockwise direction in a first axis of rotation and has a rectangular-shaped swiveling bracket attached to one edge of the swivel mount. The swiveling bracket can have a hollow cylindrical shaped end that attaches to an aperture in one end of the clip body with a retaining pin, thereby allowing the clip body to rotate about the rectangular member in a clockwise and/or counterclockwise direction in a perpendicular second axis of rotation. The mounting bracket attaches to one side of a case for a portable electronic device. The clip body further comprises a circular aperture with a notch on one portion of the clip body so that the clip body can be removably coupled to a mounting device that attaches to a surface with pressure-sensitive adhesive applied to a first side of the mounting device. The mounting device comprises a cylindrical-shaped button coupled to a second side of the mounting device, wherein the button comprises a protrusion that engages the aperture with the notch on the clip body.

In another embodiment of the present invention, there is provided a system for carrying a portable device comprising an elongated clip body formed into a U-shape with a first elongated leg extending parallel to a second elongated leg. The clip body can be attached to an article of clothing such as a belt or waistband. The system further comprises a swiveling bracket, wherein a first end of the swiveling bracket is coupled to the clip body by a retaining pin that allows the swiveling bracket to rotate about the clip body in a clockwise and/or a counterclockwise direction within a first plane. The system further comprises a mounting bracket coupled to a second end of the swiveling bracket opposite from the first end that allows the mounting bracket to rotate about the swiveling bracket in a clockwise and/or a counterclockwise direction within a second plane. The second plane is perpendicular to the first plane. The system further comprises a case for the portable device that is removably attached to the mounting bracket such that the mounting bracket and the case can rotate together within the first plane and the second plane. The first end of the swiveling bracket can be rotated about the clip body in the first plane to an acute angle such that an edge of the first elongated leg distal from the closed end of the clip acts as a stand for the case when the edge of the clip body is placed on a horizontal surface. The mounting bracket and the case can be rotated within the second plane to a landscape and a portrait position.

In yet another embodiment of the present invention, there is provided a belt clip assembly comprising an elongated clip body formed into a U-shape with a first elongated leg extending parallel to a second elongated leg. The clip body can be attached to an article of clothing worn by a person. The belt clip assembly further comprises a swiveling bracket, wherein a first end of the swiveling bracket is coupled to the clip body by a retaining pin that allows the clip body to rotate about the swiveling bracket in a first axis of rotation. The belt clip assembly further comprises a mounting bracket coupled to a second end of the swiveling bracket opposite from the first end that allows the clip body to rotate about the mounting bracket in a second axis of rotation. The second axis is perpendicular to the first axis of rotation. The mounting bracket can be removably coupled to a case for a portable device.

A more complete understanding of the belt clip apparatus will be afforded to those of skill in the art, as well as a realization of additional advantages and objectives thereof, by a consideration of the following detailed description of the preferred embodiment. Reference will be made to the appended sheets of drawings which will first be described briefly.

BRIEF DESCRIPTION OF THE DRAWINGS

FIG. 2A is a top perspective view of a mounting device used to secure the belt clip to a surface in accordance with one embodiment of the present invention.

FIG. 2B is a side perspective view of a mounting device illustrated in FIG. 2A.

FIG. 3 is a perspective view of the belt clip assembly illustrated in FIG. 1 in a pivoted position in accordance with one embodiment of the present invention.

DETAILED DESCRIPTION OF THE PREFERRED EMBODIMENT

The present invention provides a belt clip for a portable electronic device (e.g., a music player, video player, personal digital assistant, cell phone, etc.) that both swivels and pivots on two different axes. One advantage of such a clip is that the user can easily view the screen and access the controls of the electronic device without having to remove the electronic player from the user's belt. The following embodiments of the invention describe elements comprised of particular materials and colors, as well as describing particular directions and ranges of degrees of rotation of various elements that are illustrative only. These embodiments are not to be considered limiting in any respect. In the detailed description that follows, like element numerals are used to indicate like elements appearing in one or more of the figures.

Figure 1:
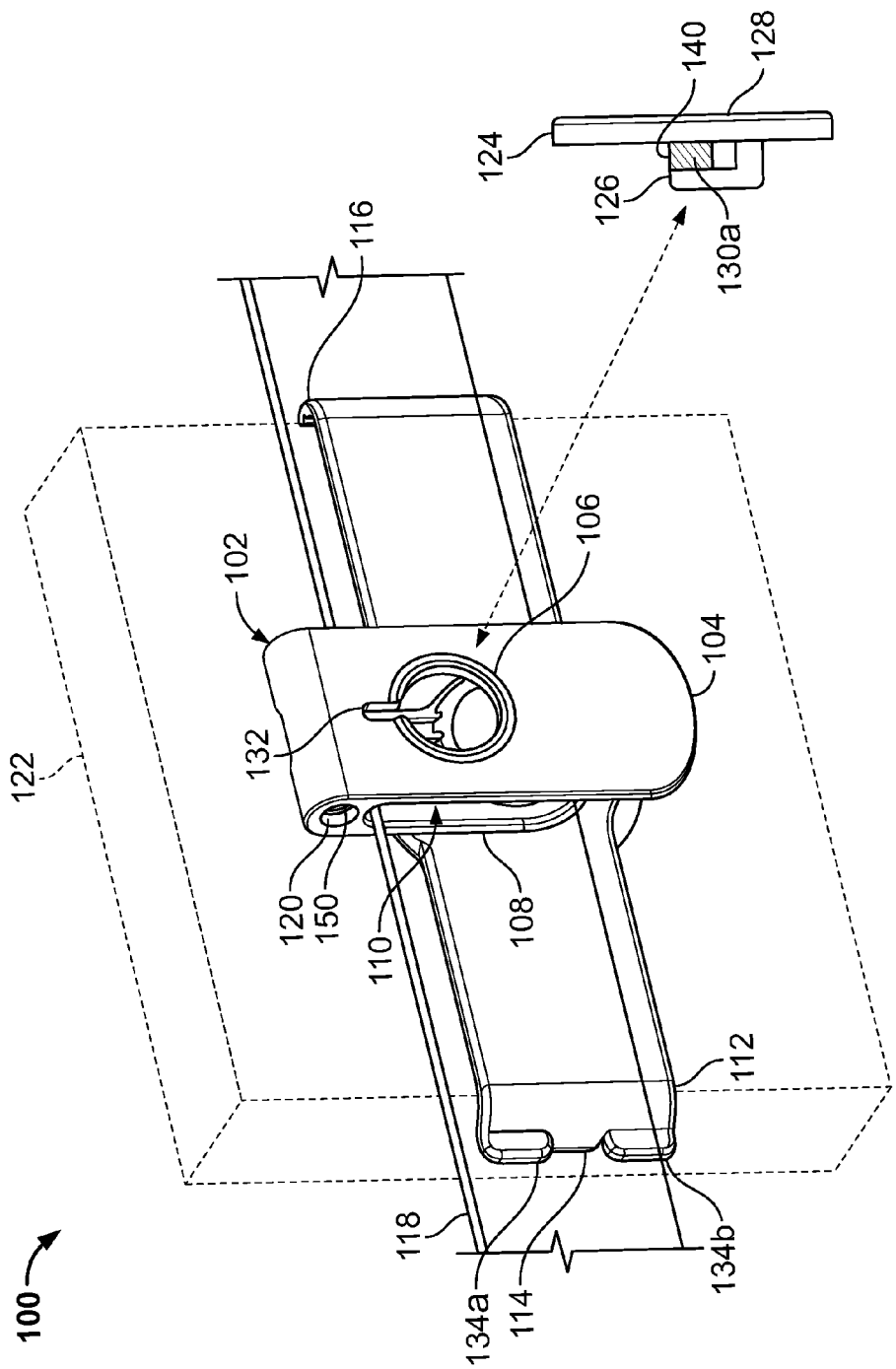
FIG. 1 is a perspective view of belt clip assembly attached to the back of a case that holds and protects a portable electronic device mounted therein in accordance with one embodiment of the present invention.

FIG. 1 is a perspective view of a belt clip or clip body 102, worn on a user's belt or article of clothing 118, and attached to the back of a case 122 that holds and protects a portable electronic device (not shown) mounted therein in accordance with one embodiment of the present invention. System or belt clip assembly 100 comprises the clip body 102 and a mounting bracket 112, and in another embodiment can also comprise a case 122 for a portable electronic device that can be mounted therein. In this embodiment, the clip body 102 comprises a front member or first elongated leg 104, a rear member or second elongated leg 108, an aperture 120, retaining pin 150, an aperture 106, a notch 132, and a slot 110. The clip body 102 utilizes the first elongated leg 104 separated from the second elongated leg 108 by the slot 110 so that the belt clip assembly 100 can be secured to a user's belt 118 by inserting the belt 118 into the slot 110. One of skill in the art will recognize that other articles of clothing or portions thereof, such as a top portion of waistband on a pair of pants or a skirt can also be inserted into the slot 110 instead of the user's belt 118. The retaining pin 150 is located within aperture 120 and enables the clip body 102 to pivot about the mounting bracket 112 in a second axis of rotation (see FIG. 4 and discussion below). The aperture 106 and notch 132 can be used to attach the clip body 102 to a mounting device 124 when the clip body 102 is not mounted on the user's belt, as described further below.

In FIG. 1, the clip body 102 is operatively connected to the center of the mounting bracket 112. The mounting bracket 112 comprises a curved first end or curved edge 116, curved second end or curved edge 114, release tabs 134a-134b, and the mounting bracket 112 that can attach to a case 122 for a portable electronic device such as a cellular phone, an mp3 music player, a video player, a portable digital assistant, and the like. In this embodiment, the case 122 is comprised of a rigid material such as plastic or metal (a "hard case"), though other materials such as a semi-rigid material like man-made or natural rubber can be utilized as well. In one embodiment, the system 100 is comprised of a substantially transparent material which offers an advantage to the user that the status of a switch or control (not shown) located on a portion of the exterior of the portable electronic device can be determined without him having to first remove the portable electronic device from the case 122 to determine the status of the switch or control.

The mounting bracket 112 can be removably coupled to the back side of the case 122 by inserting the curved first end 116 into an elongated first aperture (not shown) on the right side or first side of the case 122, followed by inserting the curved second end 114 into an elongated aperture (not shown) on the left side or second side of the case 122. To remove the mounting bracket 112 from the case 122, the user applies moderate pressure to the release tabs 134a and 134b until the mounting bracket 112 releases or "pops-off" from the case 122 (see FIG. 5 and discussion below). One skilled in the art will appreciate that other methods of removably coupling the mounting bracket 112 to the back side of the case 122 are within the spirit and scope of the present invention.

In another embodiment, the case 122 can be comprised of soft material such as leather, vinyl, silicone, etc. (a "soft case"). The mounting bracket 112 can be attached to the soft case 122 by being sewn into the back side of the case 122. One of skill in the art will appreciate that the mounting bracket 112 can be attached to the soft case 122 by other methods as well. In another embodiment (not shown), the mounting bracket 112 can be utilized to removably attach the clip body 102 directly to one side of a portable electronic device without the need for mounting the portable electronic device in the case 122.

In another variation of the embodiment shown in FIG. 1, the clip body 102 can attach to a mounting device 124. The mounting device 124 comprises button 126 with a notch or groove 130a, tab 140, and a pressure-sensitive adhesive or adhesive backing 128 applied to a flat side or back side of the base portion of the mounting device 124. A second notch or groove 130b, on the opposite side of groove 130A (visible in FIGS. 2A and 2B), together form the tab 140 at the top of the button 126. When removed from the user's belt 118, the clip body 102 can be mounted to a surface (e.g., an automobile dashboard, the side of a computer display device, a vertical wall, etc.) by attaching the mounting device 124 to the first elongated leg 104. The mounting device 124 is first securely attached to a flat portion of a surface (not shown) by removing a protective liner (not shown) from the pressure-sensitive adhesive 128 and temporarily applying pressure on the front side of the mounting device while the adhesive backing contacts the flat portion of the surface.

The mounting device 124 is generally attached to a surface that is at an angle away from a horizontal plane, but horizontal surfaces can be utilized as well, since as will be discussed below, the clip body 102 can swivel and pivot about the attached mounting bracket 112. The mounting device 124 securely attaches to the first elongated leg 104 by inserting the button 126 into the aperture 106 and rotating the clip body 102 as necessary so that the notch 132 and the tab 140 align. Gentle pressure is then applied to the clip body 102 so that the tab 132 and the notch 140 interlock with each other. One of skill in the art will recognize that other methods of removably attaching the mounting device 124 to the first elongated leg 102 are within the spirit and scope of the present invention.

The mounting device 124 can be better understood by viewing the illustrations of FIGS. 2A and 2B, which show top and side perspective views of the mounting device 124 used to secure the clip body 102 to a surface in accordance with one embodiment of the present invention. As illustrated in FIG. 2A, the base of the mounting device 124 has an elliptical or oval shape, but other shapes can be used in other embodiments as well. The components that comprise the mounting device 124 can be made of semi-rigid or rigid materials such as plastic, rubber, or metal. In FIG. 2A, the mounting device 124 has a dimpled semi-spherical indentation 202 in the top surface of the button 126, though other configurations of the top portion of the button 126 can be utilized as well.

In FIG. 2B, the button 126 has a T-shape with the notches 130a and 130b cut into the sides of the otherwise cylindrically shaped button 126 that form the tab 140. The top portion of the button 126 appears flat. The advantage of this configuration is that the button 126 can be inserted further into the aperture 106 than the button 126 would if configured differently with for example, a dome-shaped top portion. Thus, the current configuration illustrated in FIG. 2B, enables the button 126 to securely interlock with the first elongated leg 104 (see FIG. 1). One of skill in the art will however recognize that the button 126 can be shaped differently and can function without the indentation 202 as well, as long as the aperture 106 is of a compatible shape.

FIG. 3 is a perspective view of the clip body 102 in a pivoted position in accordance with one embodiment of the present invention. In this illustration, additional components that comprise the clip body 102 are visible, namely, a swivel mount 302 and semicircular edges 304a and 304b. The semicircular edges 304a and 304b have beveled edges that add stability to the mounting bracket 112 in the area surrounding a cutout (not shown) that allows the swivel mount 302 to be attached to the mounting bracket 112. More specifically, the semicircular edges 304a and 304b prevent the mounting bracket 112 from twisting about an axis. Additionally, the semicircular edges 304a and 304b minimize the mounting bracket 112 catching or getting caught on the edge of a belt or pocket when the clip body 102 is attached or removed from the belt 118 (see FIG. 1). The swivel mount 302 allows the clip body 102 to swivel or rotate in a counterclockwise direction of up to 180 degrees from the orientation shown. In other embodiments, the range and direction of rotation of the clip body 102 can vary (e.g., clockwise rotation of up to 360 degrees).

On the back side of the mounting bracket 112, there can be a circular shaped ring (not shown) that is recessed to allow for the placement of a compliant pad (not shown) comprised of silicon, rubber, etc., that increases the friction coefficient between the mounting bracket 112 and the case 122, thereby assisting the user in attaching the mounting bracket 112 to the back side of the case 122. Other shapes of recessed areas are within the spirit and scope of the present invention. The use of the compliant pad also preloads the force applied by the user in attaching the curved second end 114, and the curved first end 116 to the apertures (not shown) on the side of the case 122, and further serves to protect the case 122 from being scratched by the mounting bracket 112 attached thereto.

In the embodiment of FIG. 3, the clip body 102 independently rotates about the mounting bracket 112 in a second axis of rotation substantially perpendicular to the first axis of rotation in a clockwise and a counterclockwise direction to a plurality of pre-determined angles or positions ("click-stops") in which an audible click sound is heard by the user as these pre-determined angles are reached. When the clip body 102 is rotated to one of the plurality of click-stops, the clip body 102 semi-locks into a particular position. That is, a greater amount of force is required to continue rotation of the clip body 102 in either the same direction or the opposite direction at one of a plurality of click-stops then when the clip body 102 is at an angle in between these click-stops. Viewed from another perspective, a swiveling bracket 402 (see FIG. 4 and discussion below) independently rotates about the mounting bracket 112 in a second plane substantially perpendicular to the first plane in a clockwise and a counterclockwise direction with a plurality of predetermined angles or positions. In one embodiment, this is accomplished by the use a circular-shaped connector with a protruding tab (not shown) that is attached to the center portion of the front side of the mounting bracket 112 and interlocks with a set of triangular-shaped detents (not shown) on the back side of the swivel mount 302 located about the circumference the swivel mount 302.

The back side of the swivel mount 302 is in physical contact with the circular-shaped connector. As the user rotates the clip body 102, the protruding tab catches in the detents at the pre-determined angles. The placement of the detents, and the number of detents located on the back side of the swivel mount 302, determine at what angles of rotation the clip body 102 can stop when rotated. The two detents located at opposing ends of the circumference of the swivel mount 302 can additionally have different shaped detents that act as stops that prevent the clip body 102 from rotating beyond a maximum amount of rotation in either a clockwise or counterclockwise direction, the placement of which is determined at the time of manufacture of the swivel mount 302. One of skill in the art will recognize that other types of connectors can be used to create the click-stop effect and to limit the maximum angles of rotation of the clip body 102 about the mounting bracket 102.

The use of the plurality of click-stops make it easy for the user to determine how much he has rotated the clip body 102 without having to remove the clip body 102 from his belt to visually observe the amount of rotation. The user can simply turn or swivel the belt clip about the mounting bracket 112 until a click sound is heard. Similarly, the user can simply rotate the clip body 102 in the opposite direction the same number of click-stops to quickly return the clip body 102 to the prior position. The use of click-stops also makes it easy for the user to reach a smaller or larger degree of rotation quickly, by the user knowing that he needs to swivel the belt clip a particular number of click-stops in a particular direction (e.g., three counterclockwise click-stops), so that the case 122 (see FIGS. 1, 4, and 5) does not dig into the top of the user's thigh when he is seated in a chair (not shown). In other embodiments, the number of click-stops available for a given amount of rotational degrees varies, or the click-stop feature is completely eliminated. Such variations regarding the click-stop feature are within the spirit and scope of the present invention.

Figure 4:
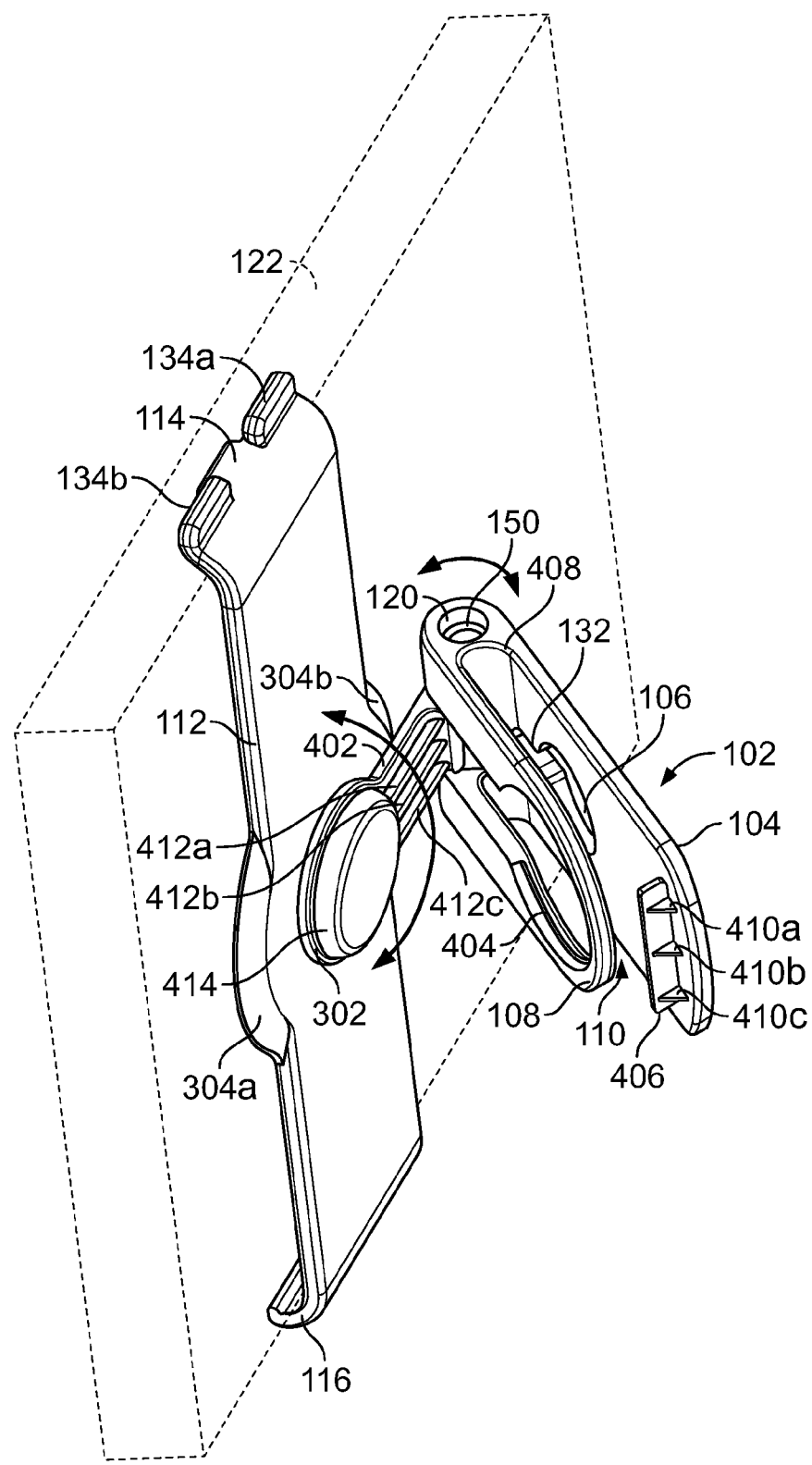
FIG. 4 is perspective view of the belt clip assembly illustrated in FIG. 1 in a fully pivoted position in accordance with one embodiment of the present invention.

The swivel mount 302 is coupled to a second end of the swiveling bracket or rectangular bracket 402 (see FIG. 4). A first end of the swiveling bracket 402 in turn is coupled to an end of the clip body 102 by retaining pin 150 located within aperture 120. The retaining pin 150 retains the swiveling bracket 402 and the clip body 102 together, yet allows the clip body 102 to rotate around the end of the swiveling bracket 402 in a first axis of rotation in a first plane in a clockwise and/or a counterclockwise direction. Viewed from another perspective, the swiveling bracket 402 can also rotate about the end of the clip body 102 in a clockwise and/or counterclockwise direction within the first plane.

As shown in FIG. 3, the clip body 102 can pivot or tilt away from the mounting bracket at an acute angle of approximately 45 degrees, though in other embodiments other pivot angles are possible. The purpose of limiting the pivot angle to approximately 45 degrees is that at this angle the belt clip reaches a rotational detent and tends to maintain this pivot angle so that the clip body 102 can act as a stand when the mounting bracket 112 is attached to the case 122 (see FIGS. 1, 4, and 5), but in other embodiments, other pivot angles can be effectively utilized. When the system 100 is utilized in such a way as a stand for a portable electronic device mounted in the case 122, a video screen, or controls on the portable electronic device, can be viewed or accessed, respectively.

To use the clip body 102 as a stand for the case 122, the first end of the swiveling bracket 402 is rotated about the end of the aperture 120 at the end of the clip body 102 in the first axis of rotation in the first plane in a counterclockwise and a clockwise direction such that a bottom edge of the case 122, and the edge of the first elongated leg 104 distal from the closed end of the clip body 102, can be placed on a horizontal surface. The swiveling bracket 402 is adapted to allow the mounting bracket 112, and the case 122, to be rotated together within the second plane in a clockwise and a counterclockwise direction to a landscape and a portrait position (see FIG. 5 and discussion below). Viewed from another perspective, the first end of the clip body 102 can also rotate about the swiveling bracket 402 in the first axis of rotation in a clockwise and a counterclockwise direction to an acute angle, such that the bottom edge of the case 122 and the edge of the first elongated leg 104 distal from the closed end of the clip body 102 can be placed on a horizontal surface. The case 122 can thus stand in a semi-vertical position in the portrait and the landscape orientation when the mounting bracket is rotated about the second axis of rotation to a corresponding position.

FIG. 4 is a perspective view of the belt clip 122 in a fully pivoted position for viewing the screen of the portable electronic device (not shown) that fits within the attached case 122 in accordance with one embodiment of the present invention. In this embodiment, the clip body 102 further comprises a swiveling bracket 402, an aperture 404 located within the second elongated leg 108, a ledge 406 perpendicular to the first elongated leg 104, and a semicircular edge 408. One end of the swiveling bracket 402 is rotatably attached to the swivel mount 302 by the retaining pin 150 and mounted within the aperture 120, as discussed with respect to FIG. 3, above. The top portion of the swivel mount 302 comprises a beveled edge 414. The beveled edge 414 allows the swivel mount 302 to be inserted easily within the aperture 404 when the clip body 102 is rotated about the aperture 120, but in other embodiments, the swivel mount 102 functions without having the beveled edge 414.

Visible in FIG. 4 is the ribbed texture of the swiveling bracket 402. More specifically, bracket 402 comprises ribbed edges 412a, 412b, and 412c. The ribbed texture adds structural rigidity that prevents the swiveling bracket 402 from breaking from torsion generated when the clip body 102 is swiveled or pivoted about the mounting bracket 112. In other embodiments, the swiveling bracket 402 can have other types and patterns of ribbing instead of the configuration of the ribbed edges 412a-412c. Additionally, the ribbed edges 412a-412c can be made thicker to add torsional rigidity to the bracket 402 when the swiveling bracket 402 and the attached clip body 102 are swiveled about the mounting bracket 112 by way of the swivel mount 302.

The aperture 404 is shaped so as to correspond to the shape of the swiveling bracket 402 and the swivel mount 302 so that the clip body can be folded flat against the mounting bracket 112. That is, the clip body 102 can be pivoted to a position that is nearly flush against the mounting bracket 114 so that the second elongated leg 108 lies flat against the mounting bracket 112. This configuration is illustrated in FIG. 1. To affix the belt clip to the user's belt 118, the belt 118 is inserted into the slot 110 (see FIG. 1 and discussion above). The slot 110 is bounded by second elongated leg 108, the first elongated leg 104, the semicircular edge 408 and the ledge 406. The semicircular edge 408 and the ledge 406 assist in keeping the clip body 102 secured or retained to the belt 118 by providing contact points around the belt 118 and in particular, the ledge 406 keeps the belt clip from being accidentally removed from the belt 118 if the clip body 102 inadvertently gets bumped as the user moves around his environment.

As illustrated in FIG. 4, the ledge 406 has triangularly-shaped supports 410a-410c, though one of skill in the art will recognize that supports 410a-410c can be shaped differently, or a different number of supports can be utilized in other embodiments. Supports 410a-410c provide rigidity and strength to ledge 406 so that the ledge 406 will not be easily broken off from the first elongated leg 104 if the clip body 102 is bumped while the user has his belt 118 inserted in the slot 110, or the user removes the clip body 102 too aggressively from his belt 118.

The ability of the swiveling bracket 402 to rotate about the center of the mounting bracket 112 and the clip body 102 to independently rotate about the end of the swiveling bracket 402 allows the user to pivot and tilt the case 122 about the clip body 102 in two different axis of rotation in the first and second planes while the belt clip is attached to the belt 118 or the top of a user's waistband (see FIG. 1 and discussion above). The pivoting and tilting actions allow the user to easily access the front portion of the case 122 that can comprise a transparent portion 504 (see FIG. 5 and discussion below) and a portable device contained therein (not shown) at a variety of angles, without having to first remove the clip body 102 from the user's belt 118. The ability of the clip body 102 to rotate about the end of the swiveling bracket 402 has the advantage of allowing the case to rotate slightly away from the clip body 102 automatically when the clip body 102 is attached to the user's belt 118 and the user takes a seated position, thereby preventing the case from digging into the top of the user's thigh.

Figure 5:
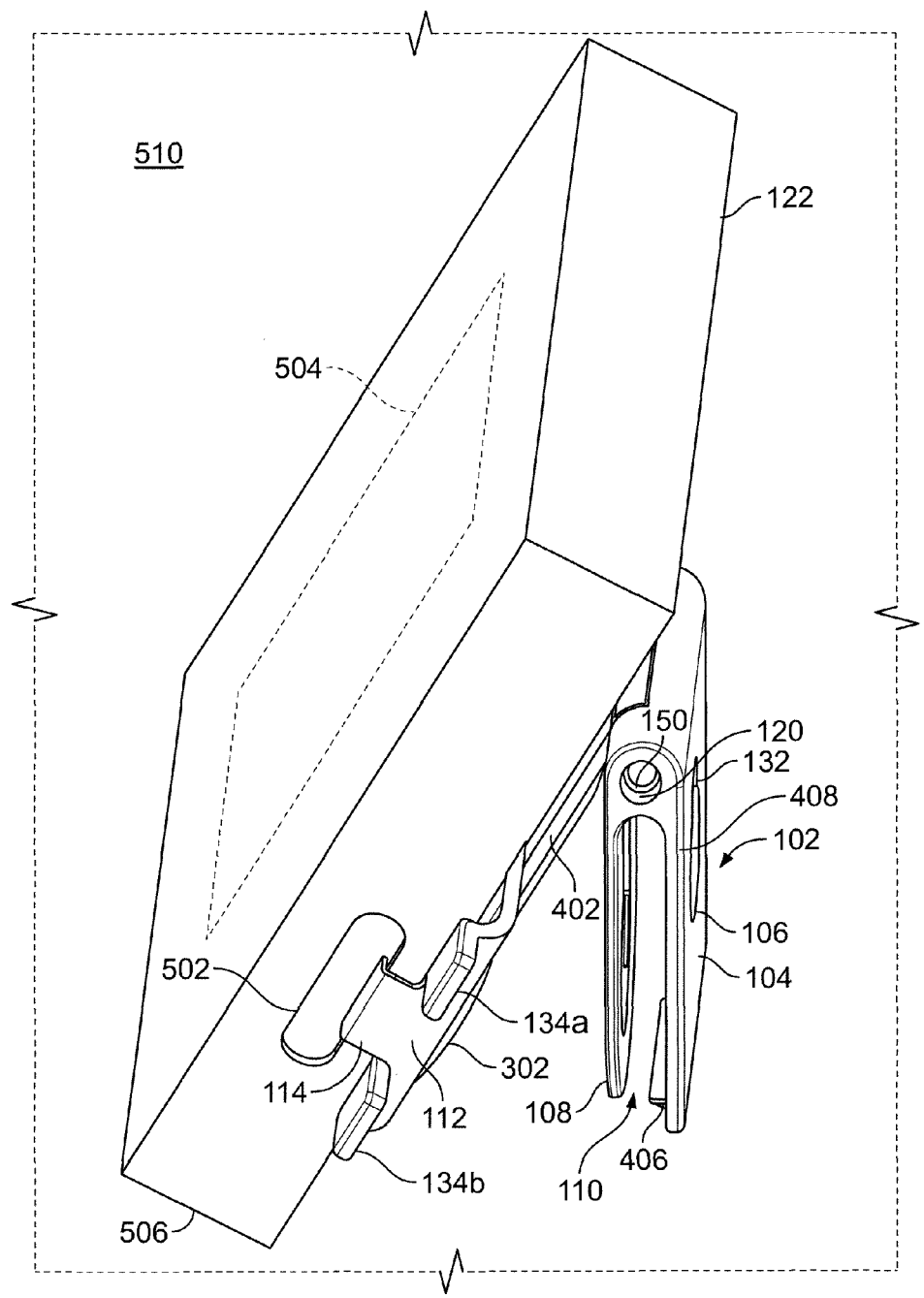
FIG. 5 is a perspective view of a belt clip assembly that can be pivoted to act as a stand for a portable electronic device in accordance with one embodiment of the present invention.

FIG. 5 is another perspective view of the clip body 102 that has been pivoted to act as a stand for the portable electronic device (not shown) that fits within the attached case 122, when placed on a horizontal surface that can be flat or curved in accordance with one embodiment of the present invention. An advantage of the present invention is that the portable electronic device can stand on a horizontal surface in both portrait and landscape modes by simply swiveling the clip body 102 in either a clockwise or counterclockwise direction of approximately ninety degrees from each other by rotating the mounting bracket about the second axis of rotation within the second plane. This feature of the present invention allows the user to select the optimal standing position of the portable electronic device mounted in the case 122 for the type of function he wants to accomplish, such as accessing music player controls or viewing a video clip. The angle between the clip body 102 and the case 122 can also be varied by rotating the belt clip about the end portion of the swiveling bracket 402 via the retaining pin 150, as discussed previously (see FIGS. 3 and 4 and discussion above). This action alters the angle between the bottom edge of the case 122 and the surface the case 122 and clip body 102 have been placed on to allow the user to optimize the viewing angle of the controls or viewing screen of the electronic device mounted within the case 122 and accessed via the transparent portion 504.

The case 122 comprises the transparent portion or window or cutout 504 that allows a viewing screen or controls of a portable electronic device mounted within the case 122 to be viewed or accessed, elliptical cutout 502, and bottom edge 506. In another embodiment, the window 504 can comprise a plurality of different sizes and shapes and the window can be made of thinner materials than other portions of the case 122 to allow the user to depress the controls of the electronic device without having to first remove the device from the case 122 to gain access. An advantage of the present invention is that the user can rotate the case 122 to either a landscape or a portrait orientation before placing the bottom edge 506 on a horizontal surface, and thereby optimize his access and/or view of the cutout 504, by first rotating the mounting bracket 112 about the second axis of rotation to one of the appropriate one of the predetermined angles (see FIG. 4 and discussion above).

In the embodiment shown in FIG. 5, the components that comprise the case 122, the clip body 102, and the mounting bracket 112 are comprised of a transparent plastic material (e.g., polycarbonate), and the retaining pin 150 is comprised of metal. In other variations of this embodiment, the case 122 is comprised of different colors of plastic and the retaining pin 150 is comprised of plastic. The invention is not limited to being comprised of plastic, and may be comprised of other materials as well. The curved second end 114 and the curved first end 116 are spaced apart from each other so that the curved second end 114 snaps into the elliptical cutout 502. The curved first end 116 similarly snaps onto an opposing elliptical cutout (not shown) on the top side of the case 122 (see FIGS. 1 and 4) in order to removably attach the mounting bracket 112 to the back side of the case 122. The user can remove the mounting bracket 112 from the back of the case 122 by grasping the tabs 134*a* and 134*b* and gently pushing on the tabs 134 and 134*b* in a direction towards the back side of the case 122. It should be appreciated by one of skill in the art that the elliptical cutout 502 and the opposing elliptical cutout on the top of the case can be shaped differently and still allow the mounting bracket 112 to be removably attached to the case 122.

In a further variation of the embodiment, the elliptical cutout 502 and the opposing elliptical cutout on the top of the case are not used, but are replaced with a plurality of suitably-shaped projecting areas (not shown) on opposing sides of the case 122 that removably couple to the curved end 114 and the curved end 116 (see FIGS. 1 and 4). Other variations in the use of the elliptical cutout 502 and the opposing elliptical cutout on the case 122 are within the spirit and scope of the present invention, such as the use of the elliptical cutout 502 on the bottom side of the case 122 and a suitably-shaped projecting area on the opposing side of the case 122 or vice versa. The ability of the mounting bracket 112 to be removably coupled to the case 122 is still retained with such variations of the embodiment.

In another embodiment, the mounting bracket 112 has a plurality of male tabs (not shown) protruding from the flat side of bracket 112 that is adjacent to the back side of the case 122. The male tabs mate with a plurality of apertures (not shown) on the back side of the case 122. In yet another embodiment, the mounting bracket 112 is permanently attached to the back of the case 122 by plastic heat weld, adhesive, or the bracket 112 can be molded together with the case 122 during the manufacturing process. One of skill in the art will recognize that other methods of either removably attaching or permanently attaching the mounting bracket 112 to the back of the case 122 are within the spirit and scope of the present invention.

Having thus described a preferred embodiment of a belt clip for a portable electronic device that can swivel and pivot with respect to a case for the portable electronic device, it should be apparent to those skilled in the art that certain advantages of the within-described system and method have been achieved. For example, the pivot feature that allows a user to view the screen or access the controls of the device (attached to the belt clip) without first removing the device from the user's belt and/or allows the belt clip to function as a stand when the player is placed on a horizontal surface has been illustrated, but it should also be appreciated that various modifications, adaptations, and alternative embodiments thereof may be made within the scope and spirit of the present invention. The invention is further defined by the following claims.

What is claimed is:

1. A system for carrying a portable device comprising:
an elongated clip body formed into a U-shape having a first elongated leg extending substantially parallel to a second elongated leg, the clip body being adapted to attach to an article of clothing worn by a person and the first and second elongated legs are substantially flat;
a swiveling bracket, wherein a first end of the swiveling bracket is coupled to the clip body by a retaining pin that allows the swiveling bracket to rotate about the clip body in at least one of a clockwise and a counterclockwise direction within a first plane;
a mounting bracket coupled to a second end of the swiveling bracket opposite from the first end that allows the swiveling bracket to rotate about the mounting bracket in at least one of a clockwise and a counterclockwise direction within a second plane, the second plane being substantially perpendicular to the first plane, and a case for the portable device removably attached to the mounting bracket such that the mounting bracket and the case are adapted to rotate together within the first plane and the second plane, wherein the first end of the swiveling bracket is further adapted to be rotated about the clip body in the first plane to an acute angle, such that an edge of the first elongated leg distal from the closed end of the clip acts as a stand for the case when the edge of the clip body is placed on a horizontal surface, the swiveling bracket being further adapted to allow the mounting bracket and the case to be rotated within the second plane to a landscape and a portrait position; and wherein the second elongated leg comprises an aperture that approximately matches a first side of the swiveling bracket allowing the elongated clip body to be rotated along the first plane until at least a portion of the first side of the swiveling bracket extends into the aperture of the second elongated leg and through the second elongated leg, and the second elongated leg of the elongated clip body folds flat against the mounting bracket.

2. The system of claim 1, wherein the mounting bracket is further adapted to allow the swiveling bracket to be rotated within the second plane to one of a plurality of a set of predetermined positions independently from rotation of the swiveling bracket in the first plane.

3. The system of claim 1, further comprising a mounting device with a pressure-sensitive adhesive adhered to a flat side of a base portion of the mounting device, allowing the mounting device to attach to a surface when pressure is applied to the mounting device, wherein the mounting device is adapted to be removably coupled to the first elongated leg, and wherein the mounting device supports the belt clip assembly.

4. The system of claim 1, wherein the clip body, the swiveling bracket, the mounting bracket, and the case are comprised of a transparent rigid material.

5. The system of claim 1, wherein the case comprises a first side with an elongated first aperture and an opposing second side with an elongated second aperture, the mounting bracket further comprises a curved first end opposed to a curved second end with a plurality of release tabs located at the second end, the curved first end is removably coupled to the elongated first aperture, and the curved second end is removably coupled to the elongated second aperture.

6. The system of claim 5, wherein the mounting bracket releases the removable coupling from the case when pressure is applied to the plurality of release tabs in a direction substantially perpendicular to the second aperture.

7. The system of claim 1, further comprising a ledge perpendicular to the first elongated leg extending toward the second elongated leg to retain the clip body around a belt.

8. The system of claim 1, wherein the case comprises at least one transparent portion that is adapted to allow the user to access at least one of a plurality of controls of a portable device when the portable device is mounted within the case, wherein the clip body is adapted to allow the user to rotate the case about the clip body in the first plane to access the at least one of the plurality of controls while the clip body is attached to the article of clothing.

9. The system of claim 8, wherein the case is adapted to be rotated about the clip body within the second plane while the clip body is attached to the article of clothing, allowing the user to select at least one of a plurality of angles of rotation within the second plane when accessing the transparent portion.

10. A belt clip assembly comprising:

an elongated clip body formed into a U-shape having a first elongated leg extending substantially parallel to a second elongated leg, the clip body being adapted to attach to an article of clothing worn by a person and the first and second elongated legs are substantially flat;

a swiveling bracket, wherein a first end of the swiveling bracket is coupled to the clip body by a retaining pin that allows the clip body to rotate about the swiveling bracket in a first axis of rotation; and a mounting bracket coupled to a second end of the swiveling bracket opposite from the first end that allows the clip body to rotate about the mounting bracket in a second axis of rotation, the second axis being substantially perpendicular to the first axis of rotation, wherein the mounting bracket is adapted to be removably coupled to a case for a portable device; and wherein the second elongated leg comprises an aperture that approximately matches a first side of the swiveling bracket allowing the elongated clip body to be rotated along the first axis of rotation until at least a portion of the first side of the swiveling bracket extends into the aperture of the second elongated leg and through the second elongated leg, and the second elongated leg of the elongated clip body folds flat against the mounting bracket.

11. The belt clip assembly of claim 10, wherein the clip body, the swiveling bracket, the mounting bracket, and the case are comprised of a transparent rigid material.

12. The belt clip assembly of claim 10, wherein the belt clip assembly further comprises a case adapted to hold a portable device.

13. The belt clip assembly of claim 12, wherein the clip body is further adapted to be rotated about the first axis of rotation to an acute angle such that an edge of the first elongated leg distal from the closed end of the clip acts as a stand for the case when the edge of the clip body is placed on a horizontal surface, the mounting bracket being adapted to be rotated about the second axis of rotation in a user selected first or a second position, the second position being approximately ninety degrees of rotation apart from the first position.

14. The belt clip assembly of claim 12, wherein the clip body is further adapted to be rotated about the first axis of rotation to an acute angle such that an edge of the first elongated leg distal from the closed end of the clip body supports a first edge of the case, allowing the case to stand in a semi-vertical position on a horizontal surface in a landscape orientation when the mounting bracket is rotated about the second axis of rotation to a corresponding position.

15. The belt clip assembly of claim 12, wherein the clip body is further adapted to be rotated about the first axis of rotation to an acute angle such that an edge of the first elongated leg distal from the closed end of the clip body supports a second edge of the case, allowing the case to stand in a semi-vertical position on a horizontal surface in a portrait orientation when the mounting bracket is rotated about the second axis of rotation to a corresponding position.

16. The belt clip assembly of claim 10, wherein the clip body is configured to rotate about the first axis of rotation in a clockwise and a counterclockwise direction.

17. The belt clip assembly of claim 10, wherein the clip body is configured to rotate about the second end of the swiveling bracket in at least one of a clockwise or a counterclockwise direction along the second axis of rotation.

18. The belt clip assembly of claim 10, further comprising a mounting device with a pressure-sensitive adhesive adhered to a flat side of a base portion of the mounting device, allowing the mounting device to attach to a surface when pressure is applied to the mounting device, wherein the mounting device is adapted to be removably coupled to the first elongated leg, and wherein the mounting device supports the belt clip assembly.

* * * * *